(12) United States Patent
Ranganathan et al.

(10) Patent No.: US 11,052,264 B2
(45) Date of Patent: Jul. 6, 2021

(54) ROBUST BROAD BEAM OPTIMIZATION FOR PROTON THERAPY

(71) Applicant: KONINKLIJKE PHILIPS N.V., Eindhoven (NL)

(72) Inventors: Vaitheeswaran Ranganathan, Bangalore (IN); Gipson Joe Anto, Kaliyal (IN); Murali Balasubramanian, Bangalore (IN); Bojarajan Perumal, Bangalore (IN); Reshmi Bhattacharjee, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 277 days.

(21) Appl. No.: 16/301,747

(22) PCT Filed: Jun. 14, 2017

(86) PCT No.: PCT/EP2017/064524
§ 371 (c)(1),
(2) Date: Nov. 15, 2018

(87) PCT Pub. No.: WO2017/216219
PCT Pub. Date: Dec. 21, 2017

(65) Prior Publication Data
US 2019/0290931 A1    Sep. 26, 2019

Related U.S. Application Data

(60) Provisional application No. 62/349,862, filed on Jun. 14, 2016.

(51) Int. Cl.
*A61N 5/10*      (2006.01)
*G21K 5/04*     (2006.01)

(52) U.S. Cl.
CPC ............... *A61N 5/103* (2013.01); *G21K 5/04* (2013.01); *A61N 2005/1087* (2013.01); *A61N 2005/1095* (2013.01)

(58) Field of Classification Search
CPC .. A61N 5/103–1039; A61N 2005/1041; A61N 2005/1087; A61N 2005/1095–1096
See application file for complete search history.

(56) References Cited

U.S. PATENT DOCUMENTS 8,340,247 B2    12/2012    Keall
2009/0304154 A1*    12/2009    Lomax ................... A61N 5/103
378/65

(Continued)

FOREIGN PATENT DOCUMENTS

WO    96/25200    8/1996
WO    2008114159    9/2008

(Continued)

OTHER PUBLICATIONS

Li et al., "Toward robust proton therapy planning and delivery", Transl Cancer Res 2012.
McGowan, et al., "Treatment planning optimisation in proton therapy 1, 2", Br J Radiol 2013.

*Primary Examiner* — Thaddeus B Cox

(57) ABSTRACT

A robustness optimization is disclosed for a broad beam proton therapy plan. A nominal dose distribution (62) is computed, to be delivered to a volume by performing proton therapy on the volume according to a proton therapy plan (50) having parameters (52) defining a range compensator shape and a range band. The parameters of the proton therapy plan are adjusted to reduce a difference between the nominal dose distribution (62) and a perturbed dose distribution calculated to be delivered to the volume modified by an error scenario (64) by performing proton therapy on the volume modified by the error scenario in accordance with the proton therapy plan with the parameters adjusted by the (Continued)

adjusting operation. The adjusting may be repeated serially for each error scenario of a set of error scenarios (44) to produce a proton therapy plan that is robust for any of these error scenarios.

19 Claims, 3 Drawing Sheets

(56) References Cited

U.S. PATENT DOCUMENTS

| | | | |
|---|---|---|---|
| 2014/0257012 A1* | 9/2014 | Hastenteufel | A61N 5/1031 600/1 |
| 2015/0038762 A1 | 2/2015 | Bert | |
| 2015/0231410 A1 | 8/2015 | Khan | |
| 2015/0335914 A1 | 11/2015 | Otto | |
| 2016/0051840 A1 | 2/2016 | Hardemark | |
| 2016/0059039 A1 | 3/2016 | Liu | |
| 2016/0287907 A1* | 10/2016 | Michaud | A61B 6/4258 |
| 2017/0266462 A1* | 9/2017 | Kesti-Helia | A61N 5/103 |

FOREIGN PATENT DOCUMENTS

| | | |
|---|---|---|
| WO | 2011/024085 | 3/2011 |
| WO | 2014/188308 | 11/2014 |
| WO | 2015/077881 | 6/2015 |
| WO | 2015103184 | 7/2015 |
| WO | 2016/070938 | 5/2016 |
| WO | 2016/207286 | 12/2016 |

\* cited by examiner

ROBUST BROAD BEAM OPTIMIZATION FOR PROTON THERAPY

CROSS REFERENCE TO RELATED APPLICATIONS

This application is the U.S. National Phase application under 35 U.S.C. § 371 of International Application No. PCT/EP2017/064524, filed Jun. 14, 2017 published as WO 2017/216219 on Dec. 21, 2017, which claims the benefit of U.S. Provisional Patent Application No. 62/349,862 filed Jun. 14, 2016. These applications are hereby incorporated by reference herein.

FIELD

The following relates generally to the proton therapy arts, broad beam proton therapy arts, proton therapy planning arts, broad beam proton therapy arts, and related arts.

BACKGROUND

Broad beam proton therapy employs a proton beam of cross-section sufficient to encompass the tumor or other planning target volume. This proton beam is generated by a proton accelerator (e.g. cyclotron or synchrotron) and homogenized over the large cross-sectional area using one or more scatterers. The homogenized beam is shaped laterally using an aperture, and is shaped in penetration depth ("range") using a range modulator and a patient-specific compensator. More particularly, the range modulator (e.g. a range modulator wheel) sets a range band (RB) which defines the proton beam modulation to produce an absorbed dose that is relatively uniform for a particular target, and the compensator is an absorbing material that reduces the maximum range to control the distal edge of the dose profile. In general, portions of the compensator that are thin produce little maximum range reduction whereas thicker compensator regions produce greater maximum range reduction. Thus, the compensator controls of the distal dose profile (within a maximum possible range determined by the upper end of the RB) while the proximal dose profile is controlled by the lower end of the RB. Viewed another way, the upper limit of the RB approximately sets the distal dose edge which is then locally fine-tuned by the compensator.

Proton therapy can provide precise conformance with a tumor or other planning target volume. For example, the distal dose fall-off for protons is very sharp, on the order of millimeters, enabling precise tumor targeting with small margins. However, this precise dose placement is also a disadvantage, in that clinically detrimental dose misplacement can result from even small errors in positioning the patient in the proton therapy apparatus, or from small shifting in internal organ positions between the time of planning image acquisition and the proton therapy session, or between successive proton therapy sessions of a fractionated proton therapy regimen (i.e., inter-fractional motion). Range uncertainty can similarly lead to detrimental dose misplacement.

The following discloses a new and improved systems and methods that address the above referenced issues, and others.

SUMMARY

In one disclosed aspect, a proton therapy planning device comprises a computer and at least one non-transitory storage medium storing instructions readable and executable by the computer to perform a proton therapy planning operations including: calculating a nominal dose distribution to be delivered to a volume by performing proton therapy on the volume according to a proton therapy plan having parameters defining at least a range compensator shape; adjusting the parameters of the proton therapy plan to reduce a difference between the nominal dose distribution and a perturbed dose distribution calculated to be delivered to the volume modified by an error scenario by performing proton therapy on the volume modified by the error scenario in accordance with the proton therapy plan with the parameters adjusted by the adjusting operation; and storing the proton therapy plan with the parameters of the proton therapy plan adjusted by the adjusting operation.

In another disclosed aspect, a proton therapy device comprises: a proton therapy planning device as set forth in the immediately preceding paragraph; and a proton beam nozzle configured to perform proton therapy on the volume in accordance with the proton therapy plan adjusted by the adjusting operation wherein said configuration of the proton beam nozzle includes at least a range compensator mounted on the proton beam nozzle whose shape is defined in accordance with the parameters adjusted by the adjusting operation defining the range compensator shape.

In another aspect, a proton therapy planning device comprises a computer and at least one non-transitory storage medium storing instructions readable and executable by the computer to perform a proton therapy planning operations including: generating a proton therapy plan with parameters defining at least a range band implemented by a range modulator device; calculating a nominal dose distribution to be delivered to a volume of a patient by performing proton therapy on the volume of the patient in accordance with the proton therapy plan; and adjusting the parameters defining the range band to improve conformance of the calculated nominal dose distribution with a planning target volume within the volume of the patient.

In another aspect, a proton therapy planning method comprises: calculating a nominal dose distribution to be delivered to a volume by performing proton therapy on the volume according to a proton therapy plan having parameters defining at least a range compensator shape; for each error scenario of a set of error scenarios, computing a difference between the nominal dose distribution and a perturbed dose distribution calculated to be delivered to the volume modified by the error scenario by performing proton therapy on the volume modified by the error scenario in accordance with the proton therapy plan; adjusting the parameters of the proton therapy plan to reduce an aggregation of the computed differences; and storing the proton therapy plan with the parameters of the proton therapy plan adjusted by the adjusting operation.

One advantage resides in providing broad beam proton therapy with improved robustness against patient positioning error.

Another advantage resides in providing broad beam proton therapy with improved robustness against range uncertainty.

Another advantage resides in providing broad beam fractionated proton therapy with improved robustness against inter-fractional organ motion deformation, bladder volume changes, rectal volume changes, or other inter-fractional changes.

Another advantage resides in providing one or more of the foregoing advantages without modifying, or with minimal modification of, the user interfacing for broad beam proton therapy planning A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
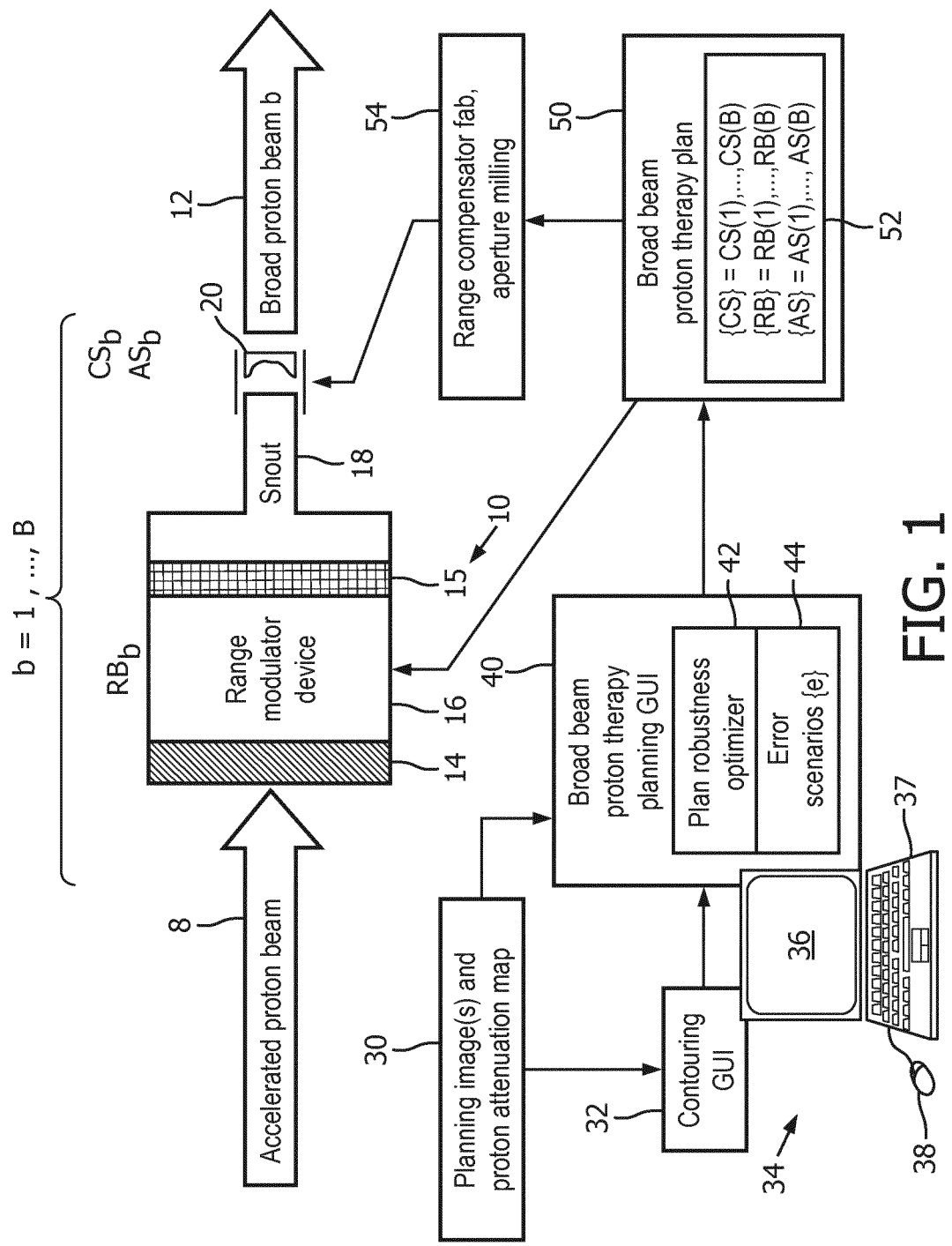
FIG. 1 diagrammatically shows a proton therapy planning apparatus along with principal components of the proton beam nozzle and attached patient-specific range compensator and beam aperture components.

With reference to FIG. 1, a proton therapy device includes a proton accelerator (e.g. cyclotron or synchrotron, not shown) that generates an accelerated proton beam 8 that is input to a proton beam nozzle 10 which manipulates the accelerated proton beam 8 to generate a broad proton beam 12 for irradiating a volume of a patient. The "volume" as used herein, includes the planning target volume (e.g., the malignant tumor intended to receive a therapeutic proton dose) and surrounding tissue which may include one or more organs at risk (OAR) whose proton dose should be limited. For delivering proton dose in a proton therapy session, as few as a single such nozzle 10 may be used to generate a single broad proton beam 12. In other proton therapy sessions two, three, or more broad proton beams may be applied in succession to deliver a tailored cumulative proton dose to the planning target volume. Without loss of generality, the number of broad proton beams serially applied in succession in a single proton therapy session is designated herein as B. This can be done with the single illustrative nozzle 10 mounted on a gantry (not shown) which allows the nozzle to be revolved about the patient to apply B proton beams in succession at B different angles. Without loss of generality, the illustrative proton beam 12 is designated as beam b (where b=1, ..., B). It is alternatively contemplated to apply multiple beams concurrently, but this would require multiple proton beam nozzles. A typical proton therapy session includes applying B beams in succession (where B=1 is contemplated) each applied to the tumor from a different angle, and the nozzle 10 is rotated from one angular position to the next to apply the B beams serially.

With continuing reference to FIG. 1, the illustrative proton beam nozzle 10 includes one or more scatterers 14, 15 (e.g., one scatterer for a single-scattering arrangement, or the illustrative two scatterers 14, 15 for a double-scattering arrangement). The purpose of the scatterers is to produce a broadened and spatially homogenized proton beam—as such, the choice between single-scatter or double-scatterer is usually determined by the needed broad beam diameter (double scattering is used for broader beams, more than two scatterers is contemplated). The scatterers may be foils, high-Z materials or solid dispersions, or so forth. A range modulator device 16, such as a range modulator wheel or a ridge filter, introduces a set of Bragg peaks in the proton beam energy spectrum that combine to form a spread-out Bragg peak (SOBP) of proton energies that is substantially flat over a range of energies that translate into a range of proton penetration depths, thus defining a range band (RB) in terms of depth over which proton dose will be deposited in the irradiated volume. For example, when using a range modulator wheel different absorbers are rotated through the beam in succession, e.g. at a rate of around 10 Hz in some devices, so that the desired (time-averaged) RB is achieved. The nozzle may include other components, such as wobbling magnets, jaw collimators, or so forth, which are not shown in diagrammatic FIG. 1. The nozzle 10 terminates in a snout 18 which provides a mounting point for patient-specific beam-shaping components 20 which typically include a range compensator for fine-tuning the distal range as a function of lateral position to conform with the distal edge of the tumor and an aperture that confines the lateral extent (i.e. cross-section) of the proton beam 12 to conform with the lateral extent of the tumor.

It should be noted that the beam-shaping components 20 (e.g. range compensator and aperture) are not only specific to the patient, but are also usually specific to the particular proton beam b being applied—thus, for a proton therapy session with B beams applied at B respective angles, there are in general B range compensator/aperture combinations, one used for each beam b where b=1, ..., B. In FIG. 1, this is diagrammatically indicated by the notation $CS_b$ which denotes the compensator shape of the $b^{th}$ range compensator. The RB provided by the range modulator device 16 is conventionally fixed; however, in some embodiments disclosed herein the RB is tailored for each beam b, i.e. the range band for the $b^{th}$ beam is denoted as $RB_b$. Thus, the proton therapy plan to be developed includes a set of compensator shapes {CS} with B elements, and a set of range bands {RB} again with B elements, and a set of aperture shapes {AS}.

The proton therapy planning process begins with acquiring one or more planning images 30 of the patient (or at least of the volume of the patient to undergo proton irradiation). For example, the planning image(s) 30 may be computed tomography (CT) images acquired by a CT scanner, or may be magnetic resonance (MR) images acquired by a magnetic resonance scanner. The planning image(s) 30 also include, or are converted to, proton beam attenuation maps of the volume to be irradiated. For CT images which can be considered to be x-ray absorption maps, this entails correcting for the difference in absorption of the x-rays versus the protons. For MR images extraction of a proton beam attenuation map may be done by segmenting the MR image to delineate different tissues and assigning to each segmented region the proton beam absorption coefficient appropriate for its tissue.

The physician, oncologist, dosimetrist, radiologist, or other medical professional operates a contouring graphical user interface (GUI) 32, for example implemented on an illustrative computer 34 including a display 36 and one or more user input devices (e.g. a keyboard 37 and mouse 38), to delineate (i.e. contour) the planning target volume (e.g. tumor) to which a proton dose is intended to be delivered. The medical professional may also delineate one or more organs at risk that lie within the volume exposed to the proton beam (or to any one of the B proton beams of the therapy session). A broad beam proton therapy planning GUI 40, also suitably implemented on the computer 34 (and of which the contouring GUI 32 may be one sub-component) is operated by the medical professional to complete the proton therapy plan. This entails, in addition to the contouring of the planning target volume and any surrounding organ(s) at risk, selecting the proton beams (e.g. the number of beams B and the angle for each beam) and various dose parameters, e.g. a minimum or target proton dose to be delivered to the planning target volume and a permissible proton dose for each organ at risk. With the dose parameters and the contours defined, an optimizer can be used to select the compensator shape $CS_b$, the range band $RB_b$, and the aperture shape $AS_b$ for each proton beam b=1, . . . , B to achieve the dose parameters within some specified tolerances. Optionally, this process may also be semi-manual or wholly manual, although this can be a time-consuming process. In general, the RB is selected to encompass the planning target volume with the lower end of the RB being chosen to be close to the proximal edge of the planning target volume, while the range compensator thickness contour is chosen to comport with the distal contour of the planning target volume. This is done taking into account the fractional proton dose contribution of each of the B proton beams. The patient-specific proton attenuation map 30 and the drawn contours are used in this process.

The output of the planning process is a proton therapy plan having parameters defining the range compensator shape and aperture shape (i.e. cross-section) for each proton beam, along with the RB for each proton beam. With these parameters designed, and taking into account the patient-specific proton attenuation as represented by the proton attenuation map 30, a dose calculator component of the broad beam proton therapy planning GUI 40 computes a nominal dose distribution to be delivered to the volume (including but usually larger than the planning target volume) by performing proton therapy on the volume according to the proton therapy plan. The medical professional reviews this nominal dose distribution to ensure it is satisfactory, and may optionally make manual adjustments, e.g. adding compensator thickness to reduce the distal edge of the proton distribution if the medical professional is concerned about inadvertent proton dosing to critical tissue at larger range. The dose calculator can be run again after such manual adjustments, and so forth, until a proton therapy plan is arrived at with its calculated nominal dose distribution.

It will be appreciated that the foregoing process does not take into account foreseeable error scenarios. For example, it may be foreseeable that the patient may be mis-positioned on the patient couch of the proton therapy delivery apparatus thus leading to a translation of the volume relative to its design-basis location. Similarly, it may be foreseeable that the urinary bladder volume at the time of the proton therapy session may be larger or smaller than the urinary bladder volume at the time of acquisition of the planning image(s) 30. It is further foreseeable that such a volumetric change could produce secondary impacts, such as distorting the tumor or other nearby organs. Another foreseeable error scenario is shifting in an internal organ position between the time of planning image acquisition and the proton therapy session, or between successive proton therapy sessions of a fractionated proton therapy regimen. These types of error scenarios are sometimes referred to as inter-fractional motion (or inter-fractional deformation, or inter-fractional volume change, or so forth), and can lead to various changes in the shape, position, and size of various organs and/or the tumor or other target volume. Yet another foreseeable error scenario is range uncertainty, which may be due to factors such as finite tolerances of the proton beam energy peak and/or spread, differences between proton absorption characteristics of the actual tissue versus the modeled absorption map, or so forth.

To address these deficiencies, the initial proton therapy plan which is calculated to produce the nominal dose distribution NDV(i) (where index i denotes voxel location) is adjusted by a plan robustness optimizer 42 to increase the robustness of the adjusted proton therapy plan against error scenarios of a set of error scenarios 44. More particularly, the plan robustness optimizer 42 increases robustness against the set of error scenarios 44 by adjusting the plan parameters, e.g. the compensator shapes and range bands $CS_b$, $RB_b$, b=1, . . . , B, so that the foreseeable error scenarios produce only a small change in the nominal dose distribution, i.e. a small change in NDV(i) summed over the volume.

A robustness-optimized proton therapy plan 50 is thus generated, including robustness optimized parameters 52. The proton therapy plan 50 including its parameters is stored, e.g. on a magnetic hard drive, solid state drive, optical disk, or so forth. In a fabrication operation 54, these optimized parameters are used to fabricate B range compensators in conformance with respective compensator shape parameters $CS_b$, b=1, . . . , B. Similarly, B apertures are fabricated in accordance with the plan aperture cross-sections (i.e. shapes) $AS_b$, b=1, . . . , B, e.g. by milling the apertures in brass plates. The proton therapy is then performed according to the robustness optimized proton therapy plan, for example by configuring the nozzle 10 at each beam angle by mounting the appropriate compensator and aperture on the snout 18 and programming the range modulator device 16 with the robustness-optimized range band parameters $RB_b$.

In the following, some illustrative embodiments of the plan robustness optimizer 42 are described in further detail. For notational convenience, the set of error scenarios 44 is denoted as {e}, and a given error scenario is denoted as e, where e∈{e}. For a given error scenario e, a corresponding dose error DE(e) can be computed as:

$$DE(e)|_{\{CS\},\{RB\}} = w_e \sum_{i \in V} (NDV(i) - PDV(i)|_{e,\{CS\},\{RB\}})^2 \quad (1)$$

where PDV (i) is the perturbed dose distribution at voxel i, that is, the proton dose that would be delivered to the voxel i if the volume is modified by the error scenario e (e.g., the volume is translated in the case of a translation error scenario, or warped in the case of a bladder volume error scenario). V denotes the volume over which the proton dose distribution is calculated—the volume V includes the planning target volume (e.g. tumor) and also surrounding tissue that receives some (preferably much lower) proton dose. The scaling parameter $w_e$ is an optional importance weight indicating the importance of the error scenario e. The different error scenarios of the set {e} may, in general, have different weights $w_e$. Thus, for example, an error scenario in which translation of the volume moves an organ at risk closer to the design-basis location of the planning target volume is likely to produce a clinically detrimental proton exposure level for that organ at risk, and so the weight $w_e$ for that error scenario is high; whereas, an error scenario of a lateral translation that does not move the organ at risk toward the high proton exposure region may be assigned a lower weight $w_e$. In an alternative embodiment, the importance weights may be applied to per-voxel differences (NDV(i)−PDV(i)$|_{e\{CS\},\{RB\}}$)$^2$ with the weight being a function of voxel position, i.e. $w_e$(i), so that Equation (1) becomes:

$$DE(e)|_{\{CS\},\{RB\}} = \sum_{i \in V} w_e(i)(NDV(i) - PDV(i)|_{e,\{CS\},\{RB\}})^2 \quad (1a)$$

Other weighting approaches may be employed. For example, regions may be assigned weights, e.g. each OAR, and the target volume, may be assigned its own weight, and/or a target volume/OAR overlap region may be assigned a (typically high) importance weight.

Equation (1) or (1a) estimates the dose error DE(e) due to a single error scenario e. The dosing error DE for the set of error scenarios {e} may be computed as an aggregation of the individual event scenario dose errors:

$$DE = \sum_{e \in \{e\}} DE(e) \quad (2)$$

In Equation (2), the optional importance weights $w_e$, if included, provide a tool for balancing the relative importance of the various error scenarios in the aggregate dose error DE. Other formulations for the aggregation are contemplated; for example, in the case of two foreseeable errors $+\Delta x$ and $-\Delta x$ where the former is a patient translation in a positive x-direction and the latter is a patient translation in opposite negative x-direction, these are mutually exclusive and so an alternatively, arguably more accurate, combination would be $\frac{1}{2}[DE(+\Delta x)+DE(-\Delta x)]$ for these two mutually exclusive error scenarios.

To improve robustness of the proton therapy plan with respect to the set of foreseeable error scenarios {e}, the plan robustness optimizer 42 suitably adjusts the parameters of the proton therapy, such as the range compensator shapes {CS}, the aperture shapes {AS}, and the range bands {RB}, so as to minimize the aggregate dose error DE, preferably with the parameters constrained to ensure the components are physically realizable. For example, the aperture shape can be no larger than the proton beam diameter or some other physical limit such as the orifice of the snout 18. Similarly, the compensator cannot at any location be thicker than the original thickness of the blank from which the compensator is fabricated (assuming the compensator is fabricated by selective thickness reduction), and the compensator can only act to reduce proton beam intensity (i.e. it cannot amplify the proton beam). In one approach, the robustness optimization is done as a single optimization problem which minimizes DE respective to the whole set of error scenarios {e}. However, this approach can be computationally difficult or even impractical, especially if the set of foreseeable error scenarios {e} and/or the number of beam B is large.

A more tractable approach entails serially adjusting the parameters of the proton therapy plan for each error scenario e of the set of error scenarios {e} to reduce the difference between the nominal dose distribution NDV(i) and the perturbed dose distribution PDV(i) calculated to be delivered to the volume modified by that error scenario. In other words, Equation (1) for a first error scenario $e_1$ is minimized by adjusting the parameters {CS,RB,AS} to minimize $DE(e_1)$ (again, preferably with constraints to ensure the resulting components are physically realizable), then Equation (1) is minimized for a second error scenario $e_2$ by further adjusting the parameters {CS,RB} to minimize $DE(e_2)$, and so forth until the entire set of error scenarios {e} has been serially processed.

One difficulty with this serial approach is that the subsequent adjustments to minimize dose error $DE(e_2)$ may increase the previously minimized dose error $DE(e_1)$, or more generally any later error scenario robustness optimization may adversely impact an earlier error scenario robustness optimization. Accordingly, after performing the serial adjusting for all error scenarios of the set of error scenarios {e}, a validation is performed in which it is checked that the aggregation of the computed differences (Equation (2)) satisfies an acceptance criterion (e.g., DE is lower than some threshold). If the validation is successful then the adjusted parameters are stored.

Figure 2:
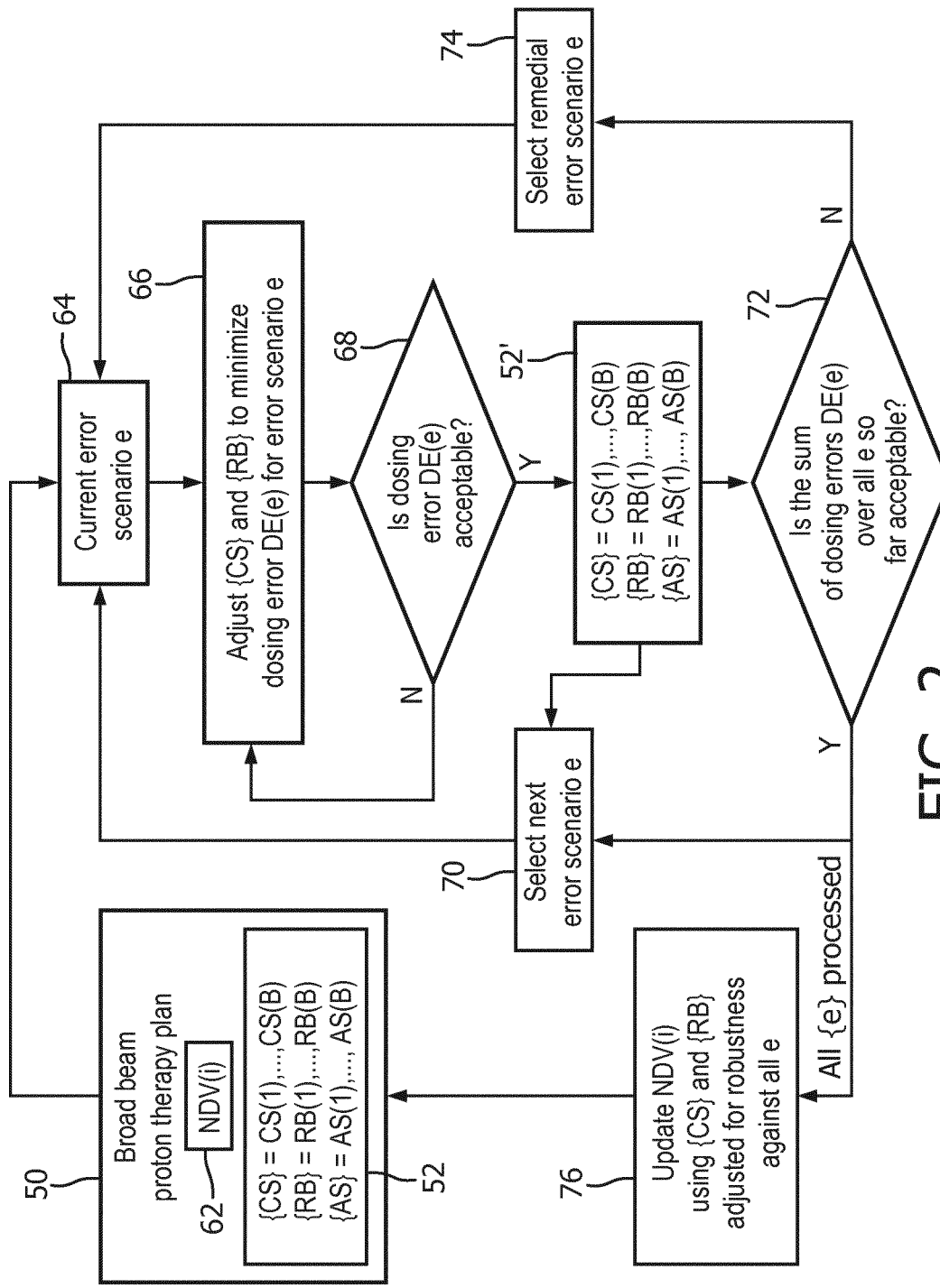
FIG. 2 diagrammatically illustrates operation of the plan robustness optimizer component of the apparatus of FIG. 1.

With reference to FIG. 2, an illustrative robust optimization that serially processes the error scenarios as just described is diagrammatically illustrated. The approach starts with the proton therapy plan 50 output by the planning GUI 40 before applying the robustness optimizer 42. This nominal plan includes the parameters 52 and the nominal dose distribution NDV(i) 62, which serves as the clinical objectives for the robustness optimization. An initial error scenario e is chosen 64 from the set of error scenarios {e}. The parameters {CS,RB} are adjusted in an operation 66 to minimize the dosing error DE(e) of Equation (1) for the error scenario e. This may be done iteratively, e.g. in a decision 68 it is determined whether the dosing error DE (e) is small enough; if not flow returns to adjustment operation 66 to further adjust the parameters to further reduce the dosing error for error scenario e. The adjusted parameters 52' are then stored, and a next error scenario is selected for processing in an operation 70. The next round of adjustment (i.e. next repetition of the adjustment operation 66) starts with the adjusted parameters 52' from the last iteration.

This serial adjustment loop 64, 66, 68, 70 may be repeated for two, three, or more error scenarios. However, as previously noted, successive iterations for each next error scenario increases the likelihood that the optimization for earlier-processed error scenarios may be so adversely affected as to no longer be acceptable. Thus, at one or more points over the serial processing of the error scenarios of the set {e}, flow may pass to an interim validation step 72, rather than directly to the next error scenario selection step 70. In the validation step 72, it is determined whether the aggregation of the dosing errors DE(e) for all error scenarios processed thus far (by the loop 64, 66, 68, 70) is acceptable.

$$DE = \sum_{e \in \{e\}|_{processed}} DE(e) \quad (3)$$

The aggregation of Equation (3) is identical with that of Equation (2) except that the summation is over only the already-processed error scenarios, denoted $e \in \{e\}|_{processed}$, rather than over all error scenarios of the set {e} as in Equation (2). Equation (3) is evaluated for the parameters {CS,RB} as adjusted by the serial processing of the already-processed error scenarios $e \in \{e\}|_{processed}$. Thus, for example, the component $DE(e_1)$ for the first error scenario $e_1$ processed by the first pass of the loop 64, 66, 68, 70 may be larger in step 72 than it was at the time of the first pass of the loop, since subsequent passes of the loop 64, 66, 68, 70 may have made adjustments to the parameters {CS,RB} that caused $DE(e_1)$ to increase. If the aggregate error of Equation (3) computed in validation step 72 is acceptable, then flow passes to the next error scenario selection step 70 to serially process the next error scenario.

On the other hand, if the aggregate error of Equation (3) computed in validation step 72 is not acceptable (i.e. the error is too large), then flow passes to a step 74 in which one of the previously processed error scenarios (that is, one of $e \in \{e\}|_{processed}$) is selected for re-processing by a repetition of the loop 64, 66, 68, 70. The error scenario selected for re-processing may, for example, be the one for which DE(e) of Equation (1) is largest. This may be repeated for each error scenario of $e \in \{e\}|_{processed}$ whose dose error DE(e) from Equation (1) is no longer acceptable, before proceeding to new error scenarios via the step 70.

When all error scenarios have been processed (or in other words $\{e\}|_{processed} \rightarrow \{e\}$) then the operation 72 serves as the final validation check to ensure that Equation (2) is satisfied. If so, then flow passes to operation 76 where the final robustness-optimized {CS,RB} parameters 52' from the last pass are stored. Additionally, up to this point the nominal dose distribution NDV(i) has been kept as it represents the clinical objectives (i.e. the dose distribution) chosen by the medical professional using the planning GUI 40. At step 76, however, this nominal dose distribution NDV(i) is preferably re-calculated using the final robustness-optimized {CS, RB} parameters 52' from the last pass. This allows the medical professional to review the updated nominal dose distribution NDV(i) generated with the robustness-optimized parameters to ensure that it is clinically acceptable before the robustness-optimized {CS,RB} parameters are stored for use in the actual proton therapy.

In the following, another example employing serial processing of successive error scenarios is described. In this example, {e} consists of six error scenarios: $+\Delta x$, $-\Delta x$, $+\Delta y$, $-\Delta y$, $+\Delta z$, $-\Delta z$ where $\Delta x$, $\Delta y$, and $\Delta z$ are translational shifts of the volume (not necessarily equal in the three orthogonal x, y, and z directions, each optionally chosen by the medical professional for a specific clinical situation). In this case, Equation (2) becomes:

$$DE = DE(+\Delta x) + DE(-\Delta x) + DE(+\Delta y) + DE(-\Delta y) + DE(+\Delta z) + \qquad (4)$$
$$DE(-\Delta z) = w_{+\Delta x} \sum_{i \in V} (NDV(i) - PDV(i)|_{+\Delta x, \{CS\}, \{RB\}})^2 +$$
$$w_{-\Delta x} \sum_{i \in V} (NDV(i) - PDV(i)|_{-\Delta x, \{CS\}, \{RB\}})^2 +$$
$$w_{+\Delta y} \sum_{i \in V} (NDV(i) - PDV(i)|_{+\Delta y, \{CS\}, \{RB\}})^2 +$$
$$w_{-\Delta y} \sum_{i \in V} (NDV(i) - PDV(i)|_{-\Delta y, \{CS\}, \{RB\}})^2 +$$
$$w_{+\Delta z} \sum_{i \in V} (NDV(i) - PDV(i)|_{+\Delta z, \{CS\}, \{RB\}})^2 +$$
$$w_{-\Delta z} \sum_{i \in V} (NDV(i) - PDV(i)|_{-\Delta z, \{CS\}, \{RB\}})^2$$

The robustness optimization minimizes the difference between the nominal and perturbed dose values for each simulated error scenario by iteratively tweaking the compensator shapes {CS} and range band parameters {RB}. In this illustrative example, the following steps are performed:

Step (a): The first isocenter shift is made to mimic one of the error scenarios out of the six (e.g., the $+\Delta x$ error scenario).

Step (b): For the current error scenario, the compensator shapes and range band (RB) parameters are iteratively adjusted for each beam b=1, . . . , B and PDV(i) is continuously updated at each voxel i by re-computing the dose at each iteration. This process gradually reduces the difference between NDV(i) and PDV(i) for the current error scenario accounting for the (optional) ROI importance weighting factors and error scenario weighting factors. In general, the compensator shape {$CS_b$} optimization for a given proton beam b allows optimizing the dose in the lateral and distal sides of the planning target volume, while the {$RB_b$} optimization allows optimizing the dose in the proximal side of the planning target volume. After optimizing the compensator shapes for the B proton beams, the respective aperture shapes {$AS_b$} are updated accordingly.

Step (c): If the resulting dose error, say DE ($+\Delta x$), is acceptable, then the current compensator shapes and RB parameters are accepted and steps (a) to (b) are repeated for next error scenario (Say, the $-\Delta x$ scenario) with the current compensator shapes and RB parameters. Again, the aperture shape is updated after the compensator shape is optimized for each error scenario.

Step (d): Once one pair of error scenarios for a single direction (say, $+\Delta x$ and $-\Delta x$) is processed, the dose error for the whole pair, namely DE($+\Delta x$)+DE($-\Delta x$) in this case, is computed with the resulting compensator shapes and RB parameters by sequentially applying the $+\Delta x$ and $-\Delta x$ isocenter shifts and re-computing dose.

Step (e): If the dose error for the pair computed in step (d) is acceptable with the current compensator shapes and RB parameters, steps (a) to (d) are executed for next error pairs (say, $+\Delta y$ and $-\Delta y$).

Step (f): On the other hand, if the dose error for the pair computed in step (d) is not acceptable with the current compensator shapes and RB parameters, then steps (a) to (d) are executed for the same pairs until the dose error for the pair computed in step (d) becomes small enough for acceptance.

Step (g): Once the compensator shapes and RB parameters are modified for all error pairs by executing steps (a) to (f), the isocenter is moved back to original position with the current compensator shapes and RB parameters and the PDV (i) are updated at each voxel i by re-computing the dose.

Step (h): If the resulting aggregate dose error in Equation (4) is acceptable, the current compensator shapes and RB parameters are accepted.

Step (i): On the other hand, if the resulting aggregate dose error in Equation (4) is not acceptable, then steps (a) to (g) are repeated until the aggregate dose error in Equation (4) becomes small enough for acceptance.

The output of this process is optimized compensator shapes, respective aperture shapes and RB parameters for each proton beam that make the proton therapy plan less sensitive to foreseeable error scenarios, while closely achieving nominal dose values at each voxel.

Figure 3:
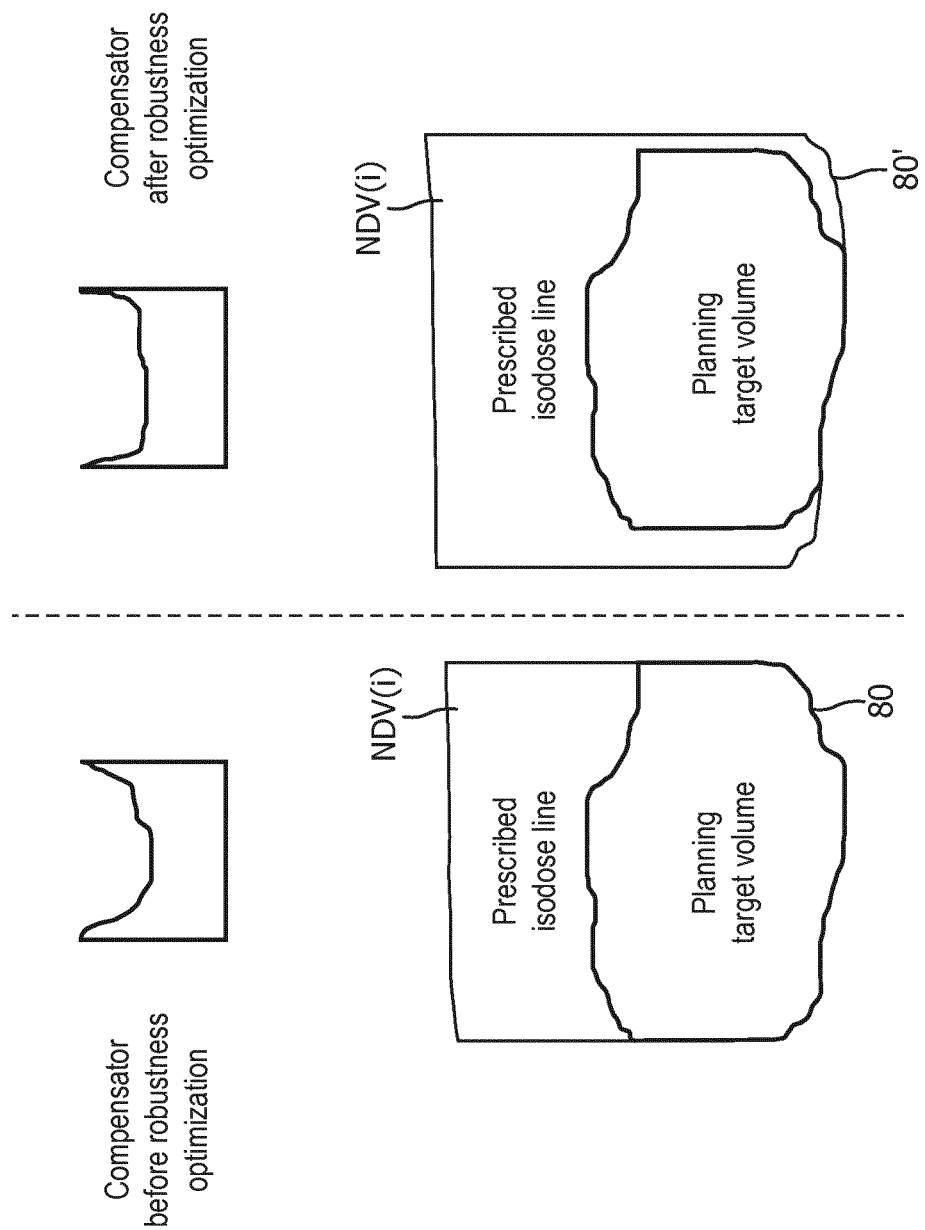
FIG. 3 diagrammatically illustrates impact of the plan robustness optimization on a distal proton dose profile.

With reference to FIG. 3, a potential effect of the robustness optimization is diagrammatically shown. The left-hand side of FIG. 3 shows the compensator shape before robustness optimization (top), and the resulting nominal dose distribution NDV(i). It will be particularly noted that a distal edge 80 of this range conforms closely with the distal edge of the planning target volume. This indeed is the clinical objective. Similarly, the aperture shape is adjusted so that the lateral extent (or sides in FIG. 3) of the prescribed isodose line coincide with the lateral extent of the planning target volume. The right-hand side of FIG. 3 shows the compensator shape after robustness optimization (top), and the resulting nominal dose distribution NDV(i). It will be noted that the adjusted distal edge 80' of this range conforms less closely with the distal edge of the planning target volume, especially at the edges. Lateral conformance is also relaxed. Although this may deviate from the ideal clinical objective of ideally perfect conformance of the proton dose distribution with the planning target volume, such relaxed conformance may be more robust against translational error scenarios. Similarly, the aperture shape is adjusted to provide some relaxation of the conformance with the sides of the planning target volume.

In some embodiments, the broad beam proton therapy planning GUI 40 displays, on the display component 36 of the computer 34, a visualization of the changes in the radiation therapy plan introduced by the plan robustness optimizer 42. For example, the broad beam proton therapy planning GUI 40 may display visualizations such as those of FIG. 3, showing the nominal dose distribution NDV(i) before the robustness optimization and the nominal dose distribution NDV(i) after the robustness optimization. Optionally, these visualizations may be rotatable three-dimensional (3D) renderings of the "before" and "after" nominal dose distributions, although other representations such as selected intersecting two-dimensional (2D) slices are additionally or alternatively contemplated. In this way, the medical professional can visually inspect the impact of the robustness optimization on the nominal dose distribution to ensure that the introduced changes in the nominal dose distribution are acceptable. For example, the adjusted distal edge 80' of the range can be inspected and compared with the originally designed range 80 of the nominal dose distribution originally to ensure the medical professional finds the less precise conformance with the distal edge of the planning target volume to be acceptable. It is also contemplated to provide a similar visualization of the compensator shape before and after the robustness optimization, e.g. visualized as a 3D rendering, so that the adjusted compensator shape can be examined to ensure any adjustments introduced by the robustness optimization do not create undue manufacturing difficulty.

As previously noted, the error scenarios can incorporate other sources of uncertainties besides translations along the x, y, and z directions, such as range uncertainty and inter-fractional organ deformational uncertainties. Other error scenarios that may be included are error scenarios in diagonal directions in the optimization process.

For example, organ deformation error scenarios may be incorporated in various ways. For instance, an organ deformations error scenarios can be specified along antero-posterior (AP), superior-inferior (SI) and medio-lateral (ML) directions, each with a (possibly different) deformation magnitude. The magnitudes of these deformations may be pre-programmed or specified by the user for a given patient based on factors such as known deformational potential of a given organ along a given anatomical direction.

In another embodiment, the error scenario may be specified by a percentage change in an existing feature—for example, the contour delineating the urinary bladder may be expanded by a certain percentage to indicate a bladder volume increase error scenario, and/or may be contracted by a certain percentage to indicate a bladder volume decrease error scenario. The percentage region-of-interest (ROI)-specific deformation representing the bladder volume change may be converted into a set of Deformation Vector Field (DVF) using a suitable elastic model (e.g. uniform displacement or damped displacement), which is applied on the contour of the bladder (ROI-warping), and/or the region of the image contained within the bladder contour (ROI density-warping) and/or the regions in the vicinity of the deformed bladder (neighborhood density-warping). This will produce warping inside the ROI as well as in the regions adjacent to the ROI. For computational efficiency, the neighborhood density-warping may be done using an "Elastic expansion-contraction model" although more complex models are contemplated. In this approach the neighborhood region is expanded if the ROI undergoes a contraction. Similarly, the neighborhood region is contracted if the ROI undergoes an expansion.

In the illustrative embodiment of FIG. 1, the plan robustness optimizer 42 is implemented by the computer 34 which also provides the user interfacing components 36, 37, 38 for the GUI modules 32, 40. For example, the computer 34 may be a desktop computer or a notebook computer. In other embodiments, the plan robustness optimizer 42 (and possibly other computationally intensive components such as the proton dose calculator component of the planning GUI 40) is implemented on a server computer, distributed computing system (e.g. cloud computing resource), or the like. Such a high-capacity computer or computing resource may be accessed by the medical professional via a desktop computer, notebook computer, or so forth. It will also be appreciated that the plan robustness optimizer 42 and other computational components may be embodied as one or more non-transitory storage media storing instruction executable by the illustrative computer 34 or by some other computer or computing resource to perform the disclosed operations. The non-transitory storage medium may, for example, comprise a hard disk or other magnetic storage medium, an optical disk or other optical storage medium, a solid state drive, flash memory or other electronic storage medium, various combinations thereof, and/or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A proton therapy device comprising:
    a computer; and
    at least one non-transitory storage medium storing instructions readable and executable by the computer to perform proton therapy planning operations including:
        calculating a nominal dose distribution to be delivered to a volume by performing broad beam proton therapy on the volume according to a broad beam proton therapy plan having parameters defining at least a range compensator shape;
        adjusting the parameters of the broad beam proton therapy plan to reduce a difference between the nominal dose distribution and a perturbed dose distribution calculated to be delivered to the volume modified by an error scenario by performing broad beam proton therapy on the volume modified by the error scenario in accordance with the broad beam proton therapy plan with the parameters adjusted by the adjusting operation, the adjusting operation being repeated for each error scenario of a set of error scenarios; and
        storing the broad beam proton therapy plan with the parameters of the broad beam proton therapy plan adjusted by the adjusting operation, repeated for all error scenarios of the set of error scenarios; and
    a proton beam nozzle configured to perform broad beam proton therapy on the volume in accordance with the broad beam proton therapy plan adjusted by the adjusting operation wherein said configuration of the proton beam nozzle includes at least a range compensator mounted on the proton beam nozzle, the range compensator having a shape defined in accordance with the parameters adjusted by the adjusting operation defining the range compensator shape.

2. The proton therapy device of claim 1 wherein the parameters of the broad beam proton therapy plan further define a range band implemented by a range modulator device.

3. The proton therapy device of claim 1 wherein the proton therapy planning operations further include:
displaying, on a display component of the computer, a visualization of the perturbed dose distribution calculated to be delivered to the volume by performing broad beam proton therapy on the volume in accordance with the broad beam proton therapy plan adjusted by the adjusting operation.

4. The proton therapy of claim 1 wherein the parameters of the broad beam proton therapy plan further define a proton beam aperture cross-section.

5. The proton therapy device of claim 1 wherein the proton therapy planning operations further include, after repeating the adjusting operation for at least two different error scenarios of the set of error scenarios:
calculating an aggregation of the differences between the nominal dose distribution and each perturbed dose distribution calculated to be delivered to the volume modified by each error scenario of the at least two different error scenarios with the parameters adjusted by the adjusting operation repeated for each of the at least two different error scenarios wherein each difference of the aggregation is weighted by a corresponding weighting factor.

6. The proton therapy device of claim 5 wherein, conditional upon the aggregation of the differences exceeding a threshold, the adjusting operation is repeated for at least one error scenario of the at least two different error scenarios.

7. The proton therapy device of claim 5 wherein the difference between the nominal dose distribution and each perturbed dose distribution is calculated as a sum of per voxel or per-region differences and the weighting factor corresponding to the difference is applied to the per voxel or per-region differences and is a function of voxel or region position.

8. The proton therapy device of claim 5 wherein the set of error scenarios includes a plurality of translational error scenarios wherein the volume modified by each translational error scenario is translated by a direction and by a distance both defined by the translational error scenario.

9. The proton therapy device of claim 5 wherein the set of error scenarios includes a feature volume error scenario wherein the volume modified by the feature volume error scenario has the volume of a feature comprising an organ or tumor or lesion at least partially within the volume changed by an amount defined by the feature volume error scenario.

10. The proton therapy device of claim 5 wherein the set of error scenarios includes an organ movement error scenario wherein the volume modified by the organ movement error scenario has an organ at least partially within the volume moved in a direction and by a distance both defined by the organ movement error scenario.

11. The proton therapy device of claim 1 wherein the broad beam proton therapy plan includes a plurality of proton beams and the parameters of the broad beam proton therapy plan define at least a range compensator shape for each proton beam.

12. A proton therapy device comprising:
a computer; and
at least one non-transitory storage medium storing instructions readable and executable by the computer to perform proton therapy planning operations including:
generating a broad beam proton therapy plan with parameters defining at least a range band implemented by a range modulator device;
calculating a nominal dose distribution to be delivered to a volume of a patient by performing broad beam proton therapy on the volume of the patient in accordance with the broad beam proton therapy plan; and
adjusting the parameters defining the range band to improve conformance of the calculated nominal dose distribution with a planning target volume within the volume of the patient, the adjusting operation being repeated for each error scenario of a set of error scenarios; and
a proton beam nozzle configured to perform broad beam proton therapy on the volume in accordance with the broad beam proton therapy plan including programming a range modulator device with the adjusted parameters defining the range band.

13. The proton therapy device of claim 12 wherein the parameters of the broad beam proton therapy plan further include parameters defining a shape of a range compensator and the proton therapy planning operations further include:
adjusting the parameters defining the shape of the range compensator to improve conformance of the calculated nominal dose distribution with the planning target volume within the volume of the patient;
wherein the proton beam nozzle is further configured to perform the broad beam proton therapy on the volume in accordance with the broad beam proton therapy plan by a range compensator mounted on the proton beam nozzle, the range compensator having a shape defined in accordance with the parameters adjusted b the adjusting operation defining the range compensator shape.

14. The proton therapy device of claim 12 wherein the proton therapy planning operations further include:
adjusting the parameters defining the range band of the broad beam proton therapy plan to reduce a difference between the nominal dose distribution and a perturbed dose distribution calculated to be delivered to the volume modified by an error scenario by performing broad beam proton therapy on the volume modified by the error scenario in accordance with the broad beam proton therapy plan with the parameters adjusted by the adjusting operation.

15. A proton therapy method comprising:
calculating a nominal dose distribution to be delivered to a volume by performing proton therapy on the volume according to a proton therapy plan having parameters defining at least a range compensator shape;
for each error scenario of a set of error scenarios, computing a difference between the nominal dose distribution and a perturbed dose distribution calculated to be delivered to the volume modified by the error scenario by performing proton therapy on the volume modified by the error scenario in accordance with the proton therapy plan;
adjusting the parameters of the proton therapy plan to reduce an aggregation of the computed differences;

storing the proton therapy plan with the parameters of the proton therapy plan adjusted by the adjusting operation; and fabricating a range compensator for use in conjunction with a proton beam nozzle, the range compensator having a shape defined in accordance with the parameters adjusted by the adjusting operation defining the range compensator shape.

16. The proton therapy method of claim 15 wherein the adjusting includes:

serially adjusting the parameters of the proton therapy plan for each error scenario of the set of error scenarios to reduce the difference between the nominal dose distribution and the perturbed dose distribution calculated to be delivered to the volume modified by that error scenario; and after performing the serial adjusting for all error scenarios of the set of error scenarios, validating that the aggregation of the computed differences satisfies an acceptance criterion wherein the storing is performed conditional upon successful validating.

17. The proton therapy method of claim 15 wherein the aggregation includes weighting each difference with a corresponding weight.

18. The proton therapy method of claim 17 wherein each difference is computed as a sum of per-voxel differences between the nominal dose distribution and the perturbed dose distribution and the weight corresponding to each difference is applied to the per voxel differences and is a function of voxel position.

19. The proton therapy method of claim 15 further comprising:

displaying, on a display component, a visualization of the perturbed dose distribution calculated to be delivered to the volume by performing proton therapy on the volume in accordance with the proton therapy plan with the parameters of the proton therapy plan adjusted by the adjusting operation;

wherein the visualization includes at least one of a three-dimensional rendering of the perturbed dose distribution and a two dimensional slice intersecting the perturbed dose distribution.

* * * * *